US011389258B2

(12) United States Patent
Pennoyer

(10) Patent No.: US 11,389,258 B2
(45) Date of Patent: Jul. 19, 2022

(54) SURGICAL DRAPE INCLUDING UNROLLING MECHANISM

(71) Applicant: Covidien LP, Mansfield, MA (US)

(72) Inventor: Raymond Pennoyer, Berlin, CT (US)

(73) Assignee: COVIDIEN LP, Mansfield, MA (US)

( * ) Notice: Subject to any disclaimer, the term of this patent is extended or adjusted under 35 U.S.C. 154(b) by 1283 days.

(21) Appl. No.: 15/573,984

(22) PCT Filed: May 26, 2016

(86) PCT No.: PCT/US2016/034257
§ 371 (c)(1),
(2) Date: Nov. 14, 2017

(87) PCT Pub. No.: WO2016/196165
PCT Pub. Date: Dec. 8, 2016

(65) Prior Publication Data
US 2018/0289438 A1 Oct. 11, 2018

Related U.S. Application Data

(60) Provisional application No. 62/168,952, filed on Jun. 1, 2015.

(51) Int. Cl.
*A61B 46/10* (2016.01)
*A61B 1/00* (2006.01)
(Continued)

(52) U.S. Cl.
CPC .......... *A61B 46/10* (2016.02); *A61B 1/00142* (2013.01); *A61B 34/35* (2016.02);
(Continued)

(58) Field of Classification Search
CPC ......... A61B 46/27; A61B 46/17; A61B 46/10; A61B 34/30; A61B 34/35; A61B 1/00135;
(Continued)

(56) References Cited

U.S. PATENT DOCUMENTS

| 4,308,864 | A | | 1/1982 | Small et al. |
| 4,308,867 | A | * | 1/1982 | Roseman ............ A61F 13/2074 |
| | | | | 424/431 |

(Continued)

FOREIGN PATENT DOCUMENTS

| CN | 202036341 U | 11/2011 |
| DE | 102008017898 A1 | 12/2008 |

(Continued)

OTHER PUBLICATIONS

Indian Office Action dated Oct. 4, 2021 corresponding to counterpart Patent Application IN 201717041569.

(Continued)

*Primary Examiner* — Jocelin C Tanner

(57) ABSTRACT

Surgical drapes reliably maintain sterility in the operating room and enable easy and efficient installation on and removal from a surgical instrument, such as a surgical instrument at the end of a robotic surgical arm. The surgical drape comprises a transitional sheath such that in a deployed configuration a second end of the sheath is spaced relatively away from a first end of the sheath, and in an un-deployed configuration the second end of the sheath is spaced relatively close to the first end of the sheath. The sheath may further include a stiffening member secured to the second end, a pull member coupled to the stiffening member, and at least one access port formed in the first end of the sheath, such that each access port is adapted for the passage of surgical instruments therethrough.

10 Claims, 6 Drawing Sheets

(51) Int. Cl.
  *A61B 34/35*   (2016.01)
  *A61B 90/50*   (2016.01)
  *A61B 34/30*   (2016.01)
  *A61B 46/27*   (2016.01)
  *A61B 46/17*   (2016.01)

(52) U.S. Cl.
  CPC .......... *A61B 90/50* (2016.02); *A61B 1/00135* (2013.01); *A61B 34/30* (2016.02); *A61B 46/17* (2016.02); *A61B 46/27* (2016.02)

(58) Field of Classification Search
  CPC ..... A61B 1/00142; A61B 90/50; A61B 19/12; A61B 19/081; A61B 46/23; A61B 46/13; A61B 46/00
  See application file for complete search history.

(56) References Cited

U.S. PATENT DOCUMENTS

| | | | |
|---|---|---|---|
| 5,358,495 A * | 10/1994 | Lynn | .................. A61M 25/0111 604/163 |
| 5,591,119 A | 1/1997 | Adair | |
| 6,416,462 B1 | 7/2002 | Tovey et al. | |
| 6,536,636 B1 | 3/2003 | McDonniel | |
| 7,854,748 B2 | 12/2010 | Gavriely | |
| 2003/0066534 A1 | 4/2003 | Spetzler et al. | |
| 2010/0286669 A1 | 11/2010 | Greer et al. | |
| 2010/0292707 A1 | 11/2010 | Ortmaier et al. | |
| 2012/0116416 A1 | 5/2012 | Neff et al. | |
| 2013/0125901 A1 * | 5/2013 | Pitaoulis | ................. A61B 46/27 128/855 |
| 2014/0338676 A1 | 11/2014 | Marinchak | |
| 2015/0297199 A1 | 10/2015 | Nicholas et al. | |
| 2015/0347904 A1 * | 12/2015 | Gavriely | ................. H04W 4/38 706/46 |
| 2017/0265951 A1 | 9/2017 | Grover et al. | |

FOREIGN PATENT DOCUMENTS

| | | |
|---|---|---|
| JP | 3141165 B2 | 3/2001 |
| WO | 03049623 A1 | 6/2003 |
| WO | 2009027848 A2 | 3/2009 |

OTHER PUBLICATIONS

Japanese Office Action dated Feb. 20, 2020 corresponding to counterpart Patent Application JP 2017-560973.
Chinese First Office Action dated Nov. 4, 2019 corresponding to counterpart Patent Application CN 201680031934.9.
Extended European Search Report corresponding to counterpart Patent Appln EP 16804051.7 dated Dec. 20, 2018.
European Office Action dated Mar. 9, 2020 corresponding to counterpart Patent Application EP 16804051.7.
Chinese Second Office Action dated Jul. 21, 2020 corresponding to counterpart Patent Application CN 201680031934.9.
International Search Report for (PCT/US2016/034257) date of completion is Sep. 12, 2016 (3 pages).

* cited by examiner

SURGICAL DRAPE INCLUDING UNROLLING MECHANISM

CROSS-REFERENCE TO RELATED APPLICATIONS

This application is a National Stage Application of PCT/US2016/034257, filed May 26, 2016 under 35USC § 371 (a), which claims benefit of and priority to U.S. Provisional Patent Application Ser. No. 62/168,952 filed Jun. 1, 2015, the disclosures of each of the above-identified applications are hereby incorporated by reference in their entirety.

BACKGROUND

Robotic surgical systems or "Telesurgery" used in minimally invasive medical procedures may include a console or cart supporting a robot arm and a surgical instrument having an end effector that may include, for example, forceps, a stapler, or a grasping tool. The robotic arm provides mechanical power to the surgical instrument for its operation and movement. During a medical procedure, the surgeon typically operates a controller which remotely controls the motion of the surgical instruments at the surgical site from a location that may differ from the patient.

Sterile drapes are typically used to protect wounds from organisms that may be present, however the current draping techniques can be ineffective when unsterilized large specialized surgical equipment is required in the operating room, such as a robotic surgical system. Attempting to cover a robotic surgical system with traditional sterile drapes may be difficult and time consuming to install, obstruct the visibility of the surgical site, or restrict the movement of system.

Accordingly, new surgical drapes that reliably maintain sterility in the operating room and enable easy and efficient installation on and removal from surgical instruments would be desirable.

SUMMARY

A surgical drape in accordance with the present disclosure is used to create or maintain a sterile barrier for a surgical device during a surgical procedure. The surgical drape may be used to create or maintain the sterile barrier around a number of surgical tools and/or robotic surgical system and the related surgical instruments and/or drive tools associated therewith.

In accordance with an aspect of the present disclosure, there is provided a surgical drape for a surgical device, the surgical drape including a sheath, a stiffener, and a pull member. The sheath of the surgical drape includes a first closed end and a second open end adapted for surgical instruments to be inserted therein. Further, the sheath is transitionable between an un-deployed configuration, wherein the second open end is spaced relatively close to the first closed end, and a deployed configuration, wherein the second open end is spaced relatively away from the first closed end. The stiffener of the surgical drape is secured adjacent to the second open end of the sheath. The pull member of the surgical drape includes a first end coupled to the stiffener and a second free end. In accordance with the present disclosure, a length of the pull member is wrapped around the stiffener in the un-deployed configuration of the sheath and unwrapped from the stiffener in the deployed configuration of the sheath. Further, the second free end of the pull member is accessible in both the deployed and un-deployed configurations of the sheath.

In embodiments of the surgical drape, the sheath may be at least in part substantially cylindrical and the first closed end is generally hemispherical.

In further embodiments, the second open end of the sheath may be rolled onto itself towards the first closed end of the sheath in the un-deployed configuration.

The sheath may be fabricated from a flexible material.

In embodiments, the stiffener may be hourglass shaped.

The surgical drape may include a pull tab disposed at the second free end of the pull member.

In further embodiments, the surgical drape may include at least one access port formed adjacent to the first closed end of the sheath.

In embodiments, the second open end of the sheath may be biased radially inward.

In accordance with another aspect of the present disclosure, a robotic surgical assembly is provided, including a robotic arm and a surgical drape, where the surgical drape provides a sterile barrier between the robotic arm and an external environment. The surgical drape of the robotic surgical assembly includes a sheath, a stiffener, a pull member, and at least one access port. The sheath of the surgical drape includes a first closed end and a second open end adapted for the robotic arm to be inserted therein. Further, the sheath is transitionable between an un-deployed configuration, wherein the second open end is spaced relatively close to the first closed end, and a deployed configuration, wherein the second open end is spaced relatively away from the first closed end. The stiffener of the surgical drape is secured adjacent to the second open end of the sheath. The pull member of the surgical drape includes a first end coupled to the stiffener, and a second free end. In accordance with the present disclosure, a length of the pull member is wrapped around the stiffener in the un-deployed configuration of the sheath and unwrapped from the stiffener in the deployed configuration of the sheath. Further, the second free end of the pull member is accessible in both the deployed and un-deployed configurations of the sheath. The at least one access port of the surgical drape is formed adjacent to the first closed end of the sheath.

In accordance with yet another aspect of the present disclosure, a method of maintaining a sterile surgical instrument is disclosed. The method includes, providing a surgical instrument, and placing an open end of a sheath over the surgical instrument while the sheath is in an un-deployed configuration. In the un-deployed configuration of the sheath, a portion of the sheath is furled on itself. The sheath is than manually transitioned into a deployed configuration by unfurling the furled portion of the sheath, such that the sheath covers a desired portion of the surgical instrument.

In embodiments of the method of maintaining a sterile surgical instrument, the sheath may further include, a stiffener secured adjacent to the open end of the sheath, and a pull member in cooperative engagement with the stiffener. During the manual transition of the sheath into the deployed configuration, the pull member may be pulled to unfurl the furled portion of the sheath.

In further embodiments, the method may further include securing the open end of the sheath to the surgical instrument at a desired position to create a sterile barrier. The surgical instrument may be at the end of a robotic surgical arm, and manually transitioning the sheath into the deployed configuration includes unfurling the furled portion of the sheath such that the sheath covers a desired portion of the robotic surgical arm.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of the embodiment(s) given below, serve to explain the principles of the disclosure, wherein.

DETAILED DESCRIPTION

Figure 1:
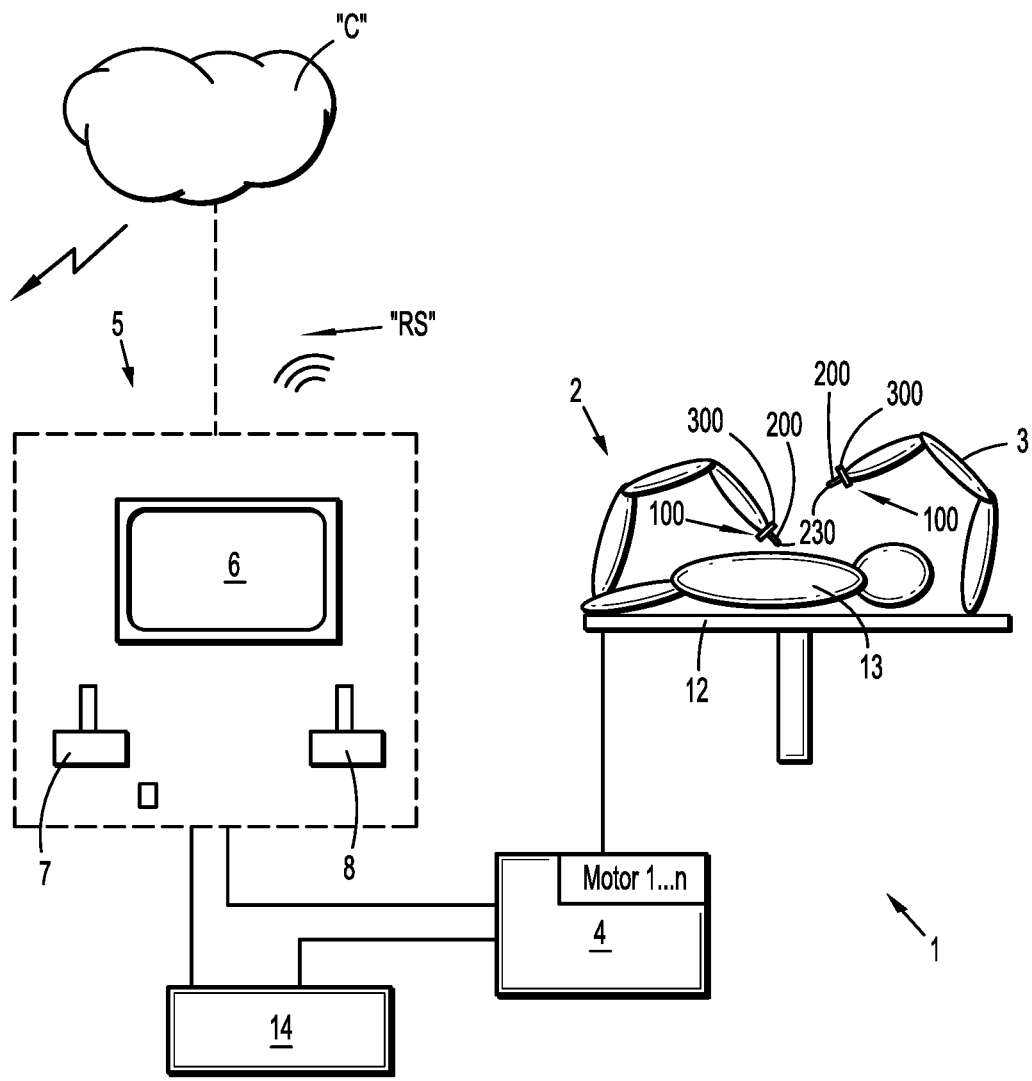
FIG. 1 is a schematic illustration of a robotic surgical system in accordance with the present disclosure.

Embodiments of the present disclosure are described in detail with reference to the drawings, in which like reference numerals designate identical or corresponding elements in each of the several views. As used herein, the term "distal" refers to that portion of a device that is farther from the user, while the term "proximal" refers to that portion of a device that is closer to the user.

While robotic surgical systems, or "Telesurgery", are discussed below, the embodiments disclosed herein may be configured to work with traditional instruments used during open surgery, minimally invasive instruments, or with any instrument or tool where a sterile barrier is desired. Only for brevity the features of the device disclosed herein will be directed towards robotic surgical systems. Robotic surgical systems employ various robotic elements to assist the surgeon and allow remote operation (or partial remote operation) of surgical instrumentation. Various robotic arms, gears, cams, pulleys, electric and mechanical motors, etc. may be employed for this purpose and may be designed with a robotic surgical system to assist the surgeon during the course of an operation or treatment. Such robotic systems may include remotely steerable systems, automatically flexible surgical systems, remotely flexible surgical systems, remotely articulating surgical systems, wireless surgical systems, modular or selectively configurable remotely operated surgical systems, etc.

The robotic surgical systems may be employed with one or more consoles that are next to the operating theater or located in a remote location. In this instance, one team of surgeons or nurses may prep the patient for surgery and configure the robotic surgical system with one or more of the instruments disclosed herein while another surgeon (or group of surgeons) remotely controls the instruments via the robotic surgical system. As can be appreciated, a highly skilled surgeon may perform multiple operations in multiple locations without leaving his/her remote console which can be both economically advantageous and a benefit to the patient or a series of patients.

With reference to FIG. 1, there is provided a robotic surgical system 1 including a plurality of robotic arms 2, 3; a control device 4; and an operating console 5 coupled with control device 4. Operating console 5 includes a display device 6, which may be set up in particular to display three-dimensional images; and manual input devices 7, 8, by means of which a person (not shown), for example a surgeon, is able to telemanipulate robotic arms 2, 3.

Each of the plurality of robotic arms 2, 3 includes a plurality of members, which are connected through joints. Robotic surgical system 1 also includes a surgical assembly 100 connected to a distal end of each of robotic arms 2, 3. Surgical assembly 100 includes an instrument drive unit 300 and a surgical instrument 200 detachably coupled to instrument drive unit 300. Surgical instrument 200 includes an end effector 230.

Robotic arms 2, 3 may be driven by electric drives (not shown) that are connected to control device 4. Control device 4 (e.g., a computer) is set up to activate the drives, in particular by means of a computer program, in such a way that robotic arms 2, 3, their surgical assemblies 100 execute a desired movement according to a movement defined by means of manual input devices 7, 8. Control device 4 may also be set up in such a way that it regulates movement of robotic arms 2, 3 and/or of the drives.

With continued reference to FIG. 1, robotic surgical system 1 is configured for use on a patient 13 lying on a patient table 12 to be treated in a minimally invasive manner by means of end effector 230. Robotic surgical system 1 may include more than two robotic arms 2, 3. The additional robotic arms may also be connected to control device 4 and may be telemanipulatable by means of operating console 5. One or more additional surgical assemblies 100 and/or surgical instruments 200 may also be attached to the additional robotic arm.

Control device 4 may control a plurality of motors (Motor 1 . . . n) with each motor configured to drive a pushing or a pulling of one or more cables (not shown) coupled to end effector 230 of surgical instrument 200. It is also contemplated that the cables can be replaced with rods or the like. In use, as these cables are pushed and/or pulled, the cables effect operation and/or movement of end effector 230 of surgical instrument 200. It is contemplated that control device 4 coordinates the activation of the various motors (Motor 1 . . . n) to coordinate a pushing or a pulling motion of one or more of the cables in order to coordinate an operation and/or movement of one or more end effectors 230. In embodiments, each motor can be configured to actuate a drive rod or a lever arm to effect operation and/or movement of end effectors 230 in addition to, or instead of, one or more cables.

Control device 4 can include any suitable logic control circuit adapted to perform calculations and/or operate according to a set of instructions. Control device 4 can be configured to communicate with a remote system "RS", either via a wireless (e.g., Wi-Fi™, Bluetooth®, LTE™, etc.) and/or wired connection. Remote system "RS" can include data, instructions and/or information related to the various components, algorithms, and/or operations of robotic surgical system 1. Remote system "RS" can include any suitable electronic service, database, platform, cloud "C" (see FIG. 1), or the like. Control device 4 may include a central processing unit operably connected to memory. The memory may include transitory type memory (e.g., RAM) and/or non-transitory type memory (e.g., flash media, disk media, etc.). In some embodiments, the memory is part of, and/or operably coupled to, remote system "RS".

Control device 4 can include a plurality of inputs and outputs for interfacing with the components of robotic surgical system 1, such as through a driver circuit. Control device 4 can be configured to receive input signals and/or generate output signals to control one or more of the various components (e.g., one or more motors) of robotic surgical system 1. The output signals can include, and/or can be based upon, algorithmic instructions which may be pre-programmed and/or input by a user. Control device 4 can be configured to accept a plurality of user inputs from a user interface (e.g., switches, buttons, touch screen, etc. of operating console 5) which may be coupled to remote system "RS".

A database 14 can be directly and/or indirectly coupled to control device 4. Database 14 can be configured to store pre-operative data from living being(s) and/or anatomical atlas(es). Database 14 can include memory which can be part of, and/or operatively coupled to, remote system "RS". Reference may be made to U.S. Patent Publication No. 2012/0116416, filed on Nov. 3, 2011, entitled "Medical Workstation," the entire content of which is incorporated herein by reference, for a detailed discussion of the construction and operation of robotic surgical system 1.

Figure 2:
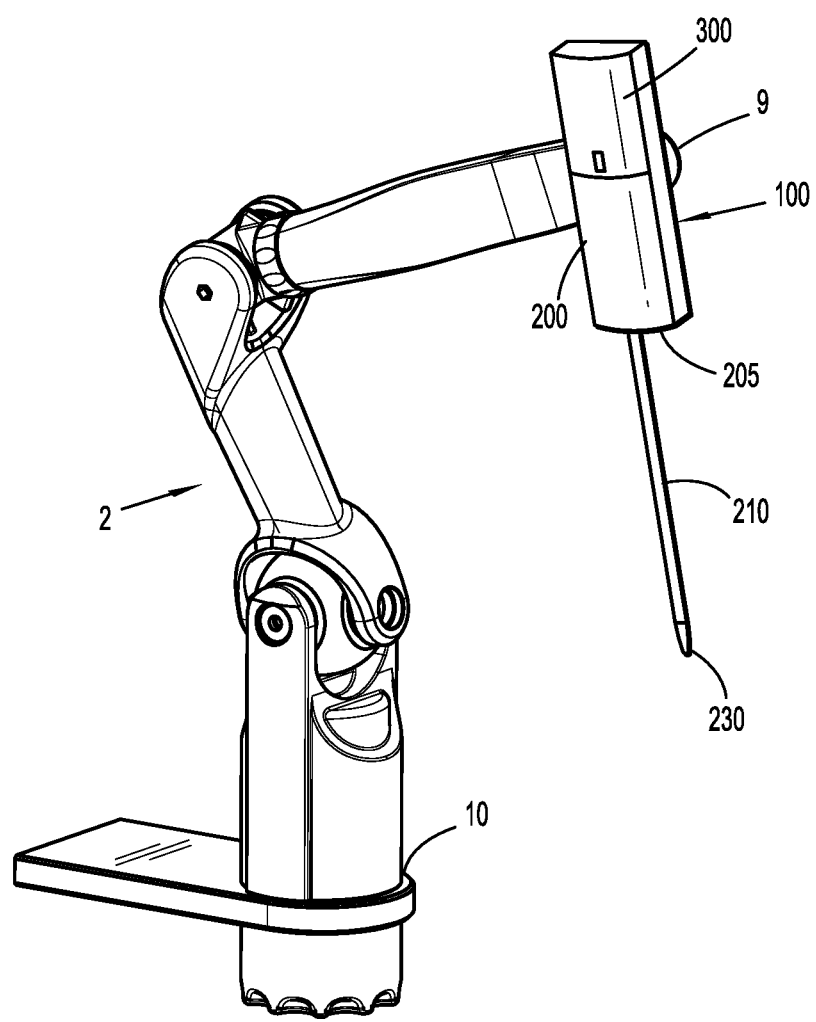
FIG. 2 is a perspective view of a robotic arm having a surgical assembly mounted thereon.

Turning now to FIG. 2, surgical assembly 100 includes instrument drive unit 300 coupled to robotic arm 2, and surgical instrument 200 releasably coupled to instrument drive unit 300. Instrument drive unit 300 includes a body which defines a cutout configured to receive an adapter portion of surgical instrument 200, such that surgical instrument 200 is detachably coupled to instrument drive unit 300. In this manner, various surgical instruments may be interchangeably used with instrument drive unit 300. For instance, U.S. patent application Ser. No. 14/257,063, filed Apr. 21, 2014 and entitled "Adapter Assembly with Gimbal for Interconnecting Electromechanical Surgical devices and Surgical Loading Units, and Surgical Systems Thereof," the entire contents of which is hereby incorporated by reference, describes surgical stapling devices with end effectors that support distally advanceable sleds operatively coupled to a rotatable lead screw to fire surgical staples. Further reference may be made to U.S. Patent Application Ser. No. 61/992,700, filed May 13, 2014 and entitled "Robotic Surgical Systems and Instrument Drive Units," the entire contents of which is hereby incorporated by reference, which describes an instrument control unit for use with a surgical instrument. Surgical instrument 200 includes an elongate member 210 and an end effector 230 disposed on a distal end. It should be appreciated that end effector 230 comes into direct contact with a patient during use of robotic surgical system 1, thereby creating a need to maintain a sterile environment with regard to surgical instrument 200, instrument driver unit 300, and robotic arm 2.

Figure 3A:
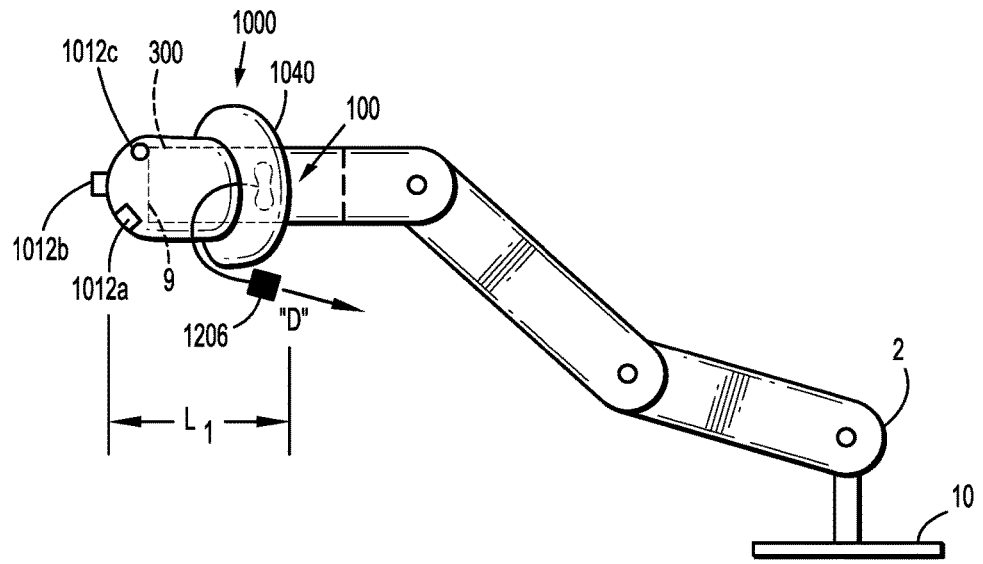
FIG. 3A is a front schematic view of a surgical drape in accordance with the present disclosure draped onto the robotic arm of FIG. 2 with the surgical drape in the undeployed configuration.
Figure 3B:
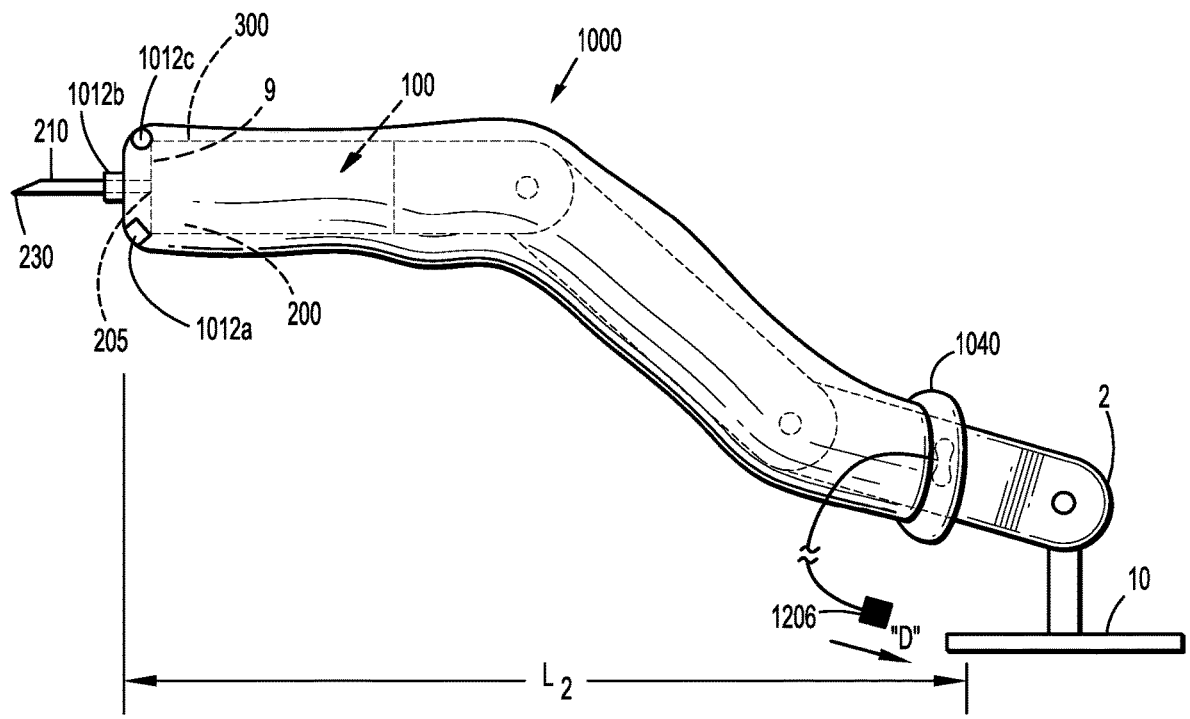
FIG. 3B is a front schematic view of FIG. 3A with the surgical drape in the deployed configuration.

With initial reference to FIGS. 3A-3B, surgical drape 1000 is shown covering or essentially enclosing surgical tools to maintain a sterile surgical environment. In use with robotic surgical system 1, surgical drape 1000 is positioned over either instrument drive unit 300 prior to mounting surgical instrument 200 to instrument drive unit 300, or positioned over both surgical instrument 200 and instrument drive unit 300 after surgical instrument 200 has been mounted to instrument drive unit 300. During use, surgical drape 1000 acts as a sterile barrier to prevent contamination of surgical instrument 200, instrument drive unit 300, and/or robotic arm 2 (e.g., from bodily fluids, ambient environment, etc.).

Surgical drape 1000 may extend along a portion of, or along the entire length of, robotic arm 2 (FIG. 3B), thereby covering surgical instrument 200, instrument driver unit 300, and robotic arm 2 to a desired location. Surgical drape 1000 may be formed from any material known in the art which provides flexibility to enable unobstructed movement of the covered surgical instruments while providing a strong tear resistant sterile barrier. For example, surgical drape 1000 may be fabricated from a flexible and/or impermeable plastic. Surgical drape 1000 may be adapted to form fit or loosely fit over components of robotic surgical system 1, e.g., surgical instrument 200, instrument drive unit 300, and/or robotic arm 2, or made to freely stretch or bend to their respective movements during use.

Figure 4:
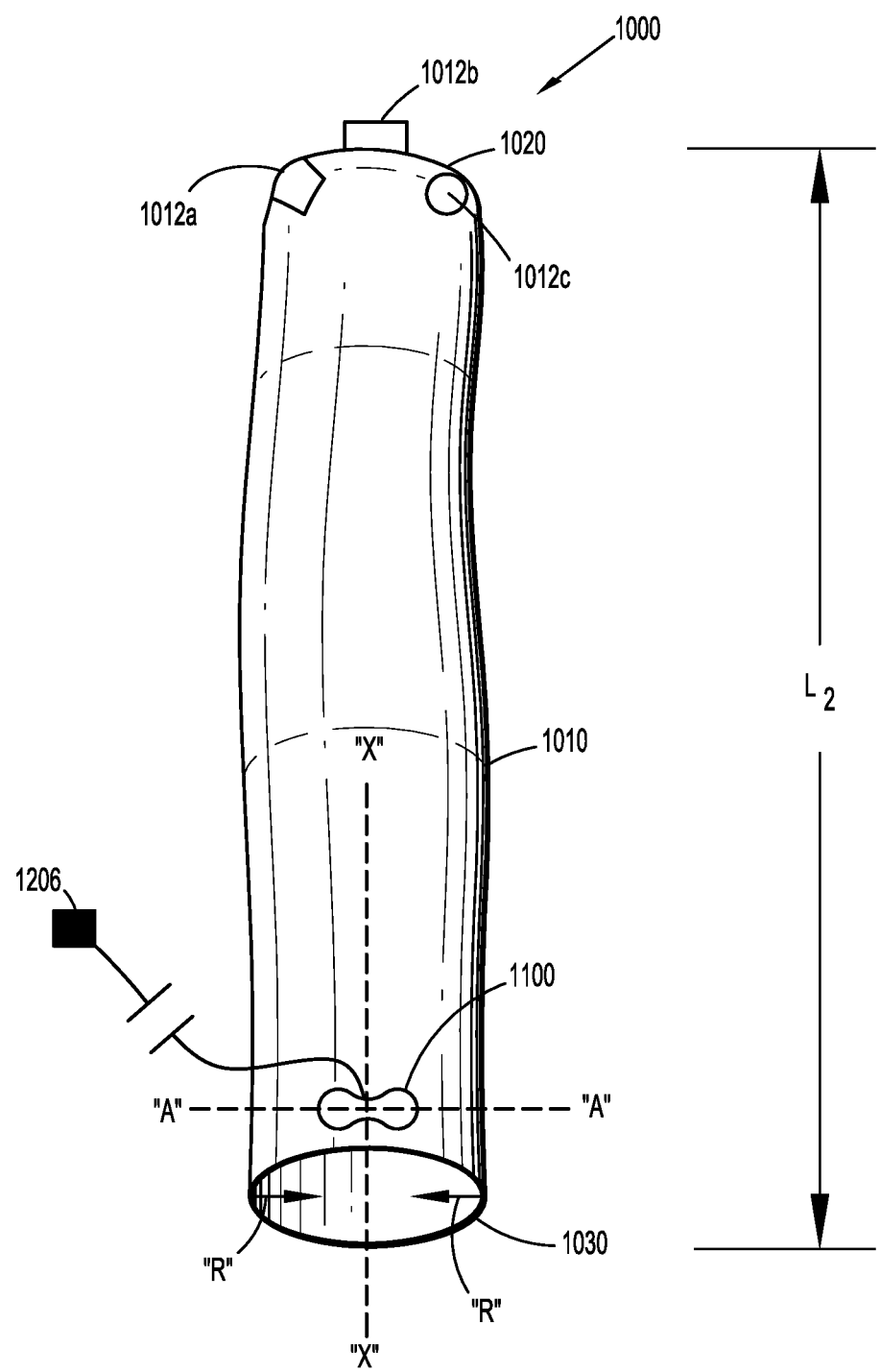
FIG. 4 is a side view of the surgical drape of FIG. 3B.
Figure 5A:
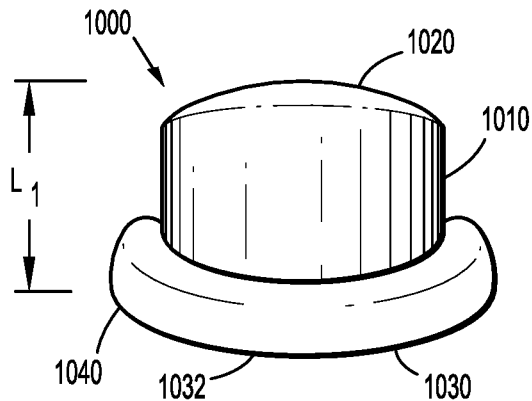
FIG. 5A is a front view of an embodiment of the surgical drape of FIG. 3A.
Figure 5C:
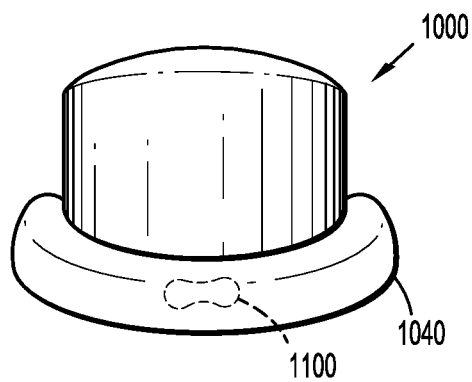
FIG. 5C is a front view of an embodiment of the surgical drape of FIG. 3A including a stiffener shown in phantom.
Figure 5B:
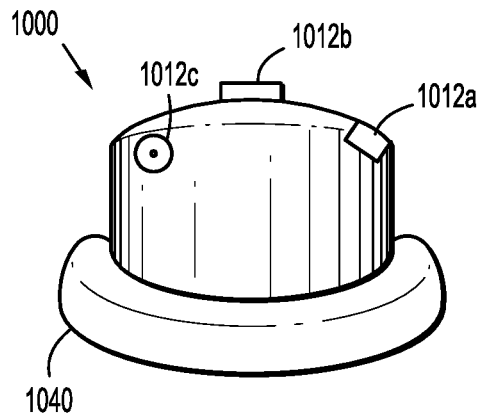
FIG. 5B is a front view of an embodiment of the surgical drape of FIG. 3A including access ports.
Figure 5D:
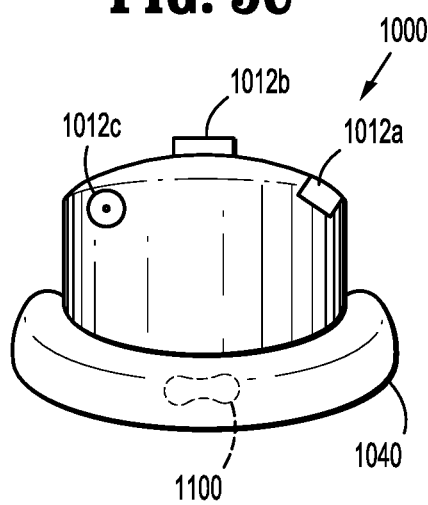
FIG. 5D is a front view of an embodiment of the surgical drape of FIG. 3A including access ports and a stiffener shown in phantom.
Figure 5E:
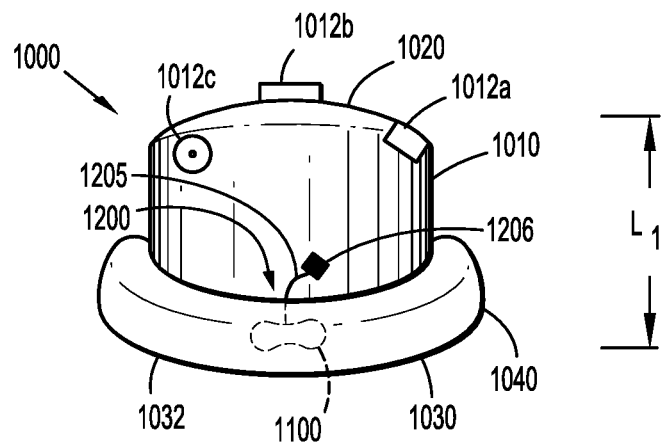
FIG. 5E is a front view of an embodiment of the surgical drape of FIG. 3A including access ports, a stiffener shown in phantom, and a pull member coupled to the stiffener.
Figure 6A:
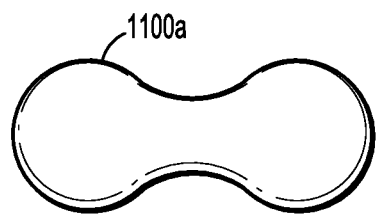
FIG. 6A is a front view of an embodiment of the stiffener of FIGS. 5C-5E in accordance with the present disclosure.
Figure 6B:
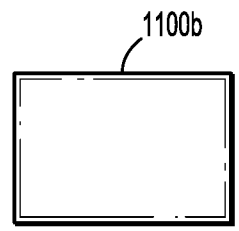
FIG. 6B is a front view of an alternate embodiment of the stiffener of FIG. 6A.
Figure 6C:
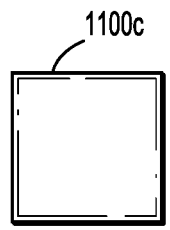
FIG. 6C is a front view of another embodiment of the stiffener of FIG. 6A.
Figure 6D:
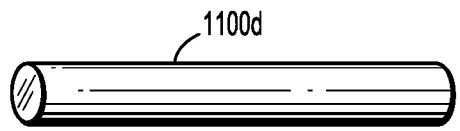
FIG. 6D is a front view of yet another embodiment of the stiffener of FIG. 6A.

With reference to FIGS. 4-5E, surgical drape 1000 includes a sheath 1010 having a first end 1020, a second end 1030, and a length therebetween. It is further envisioned that first end 1020 may be closed and generally spherical or hemi-spherical while second end 1030 defines an open cuff 1032 adapted for insertion of surgical tools therein. Additionally, sheath 1010 may further include a reinforced support (not shown) formed of, e.g., a rigid polymer sheet, at specific locations along the length and/or a circumference of sheath 1010, to provide a reinforced surface against which surgical tools and devices may impart destructive forces to sheath 1010, e.g., frictional forces, during use.

For use with robotic surgical system 1, open cuff 1032 may be shaped and dimensioned for the passage of surgical instrument 200, instrument drive unit 300, and/or a distal portion 9 of robotic arm 2 therethrough. The length of sheath 1010 may further be sized to approximately correspond to the combined length from a distal end 205 of surgical instrument 200, or distal portion 9 of robotic arm 2, to a proximal end 10 of robotic arm 2, such that surgical drape 1000 can provide a protective barrier to the entire robotic arm 2 and any surgical assemblies 100 mounted thereon.

Sheath 1010 is transitionable between an un-deployed configuration having an un-deployed length "$L_1$" (FIG. 3A) and a deployed configuration having a deployed length "$L_2$" (FIG. 3B), such that "$L_2$" is larger than "$L_1$". It should be appreciated that the deployed length "$L_2$" is user dependent and may be set at any length desired by an operator. As sheath 1010 transitions from the un-deployed configuration to the deployed configuration, and vice-versa, second end 1030 of sheath 1010 moves away from or towards first end 1020 of sheath 1010 respectively. It is envisioned that second end 1030 of sheath 1010 may rollably transition between the un-deployed configuration to the deployed configuration, and vice-versa. As the second end 1030 of sheath 1010 is rolled towards the first end 1020 of sheath 1010, sheath 1010 also rolls towards front end 1020 such that the sheath is furled over the second end 1020 and the deployed length "$L_2$" is reduced, forming a rolled sheath portion 1040 about the second end 1020. In use, an operator may manually extend and transition the sheath 1010 into the deployed configuration by moving, rolling, or unfurling the second end 1030 away from first end 1020.

Sheath 1010 may further include an access port 1012 disposed on a surface of sheath 1010 designed to permit passage of surgical instruments therethrough while maintaining a sterile barrier. Access port 1012 may be sized and dimensioned for passage of a variety of surgical instruments, including but not limited to, end effectors, graspers, cutters, scissors, staplers, retractors, etc. As seen in FIG. 5B, it is envisioned that there may be a plurality of access ports 1012a-c of differing sizes and dimensions provided on sheath 1010 to accommodate a wide variety of surgical instruments. Once such instrument is shown in FIG. 3B, where end effector 230 and elongate member 210 of surgical instrument 200 passes through access port 1012a such that a sterile barrier is formed at the access port.

With reference to FIGS. 3A-4 and 5C-5E, surgical drape 1000 may further include at least one stiffener 1100 disposed on the second end 1030 of sheath 1010. Each stiffener 1100 may be adhered to an outer surface of sheath 1010, in or near second end 1030 of sheath 1010. As seen in FIG. 4, a longitudinal axis "A" of stiffener 1100 is generally transverse to a longitudinal axis "X" of sheath 1010. During the transition between the deployed and un-deployed configurations, stiffener 1100 cooperatively moves with the second end 1030 of sheath 1010, such that the second end 1030 is rolled about the stiffener 1100 away from and towards the first end 1020. As the second end 1030 is rolled about the stiffener 1100 it should be appreciated that a portion of sheath 1010 is also rolled or furled about stiffener 1100, forming the rolled sheath portion 1040 with stiffener 1100 and second end 1030 of sheath 1010 at the middle of the rolled sheath portion 1040.

As seen in FIGS. 6A-6D, stiffener 1100 may take a variety of forms such as, for example, an hour glass shape 1100a (FIG. 6A), a rectangular shape 1100b (FIG. 6B), a square shape 1100c (FIG. 6C), or a tubular shape 1100d (6D), or any variation of the above. Stiffener 1100 serves to provide structural support for surgical drape 1000 such that when transitioning between the deployed and un-deployed configurations the cuff 1032 of sheath 1010 is not closed or obstructed.

Figure 7A:
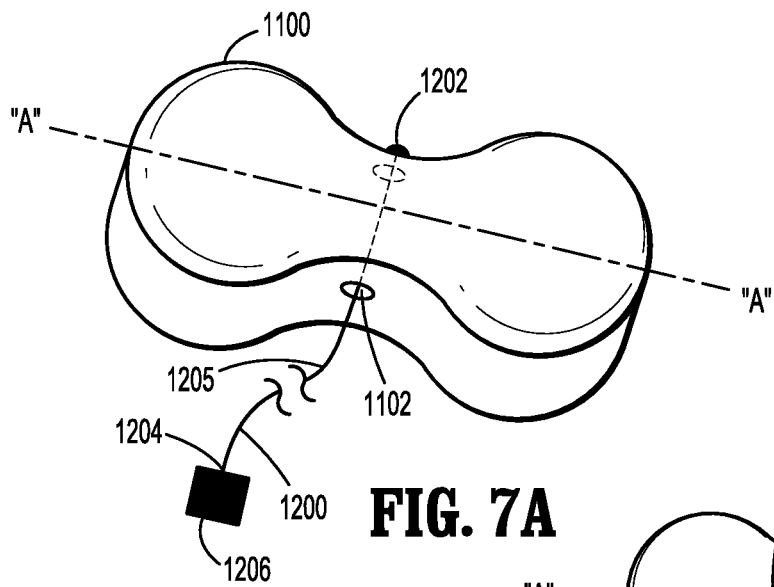
FIG. 7A is a front perspective view of the stiffener of FIG. 6A coupled to the pull member of FIG. 5E.
Figure 7B:
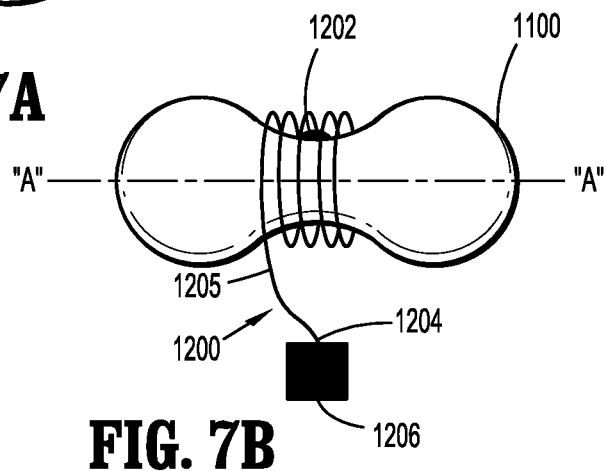
FIG. 7B is a front view of the stiffener of FIG. 7A with the pull member rolled about the stiffener.

With reference to FIGS. 7A and 7B, stiffener 1100 may be coupled to a pull member 1200. In embodiments wherein there are multiple stiffeners 1100, each stiffener 1100 is coupled to a respective pull member 1200. Pull member 1200 includes a first end 1202, a second end 1204, and a length 1205 therebetween, where the first end 1202 is coupled to the stiffener 1100. Pull member 1200 may be coupled to stiffener 1100 through borehole 1102, or through any other suitable means known in the art, e.g., adhered, glued, tied, taped, stapled, etc. As seen in FIG. 7B, the length 1205 of pull member 1200 may be wrapped around the longitudinal axis "A" of stiffener 1100 when second end 1030 of sheath 1010 is rolled-up or furled forming the rolled sheath portion 1040, such that the second end 1204 extends from the stiffener. Pull member 1200 may further include a tab 1206 disposed at the second end 1204.

It should be appreciated that pull member 1200, stiffener 1100, and the second end 1030 of sheath 1010 act cooperatively to aid users in transitioning surgical drape 1000 from the un-deployed configuration to the deployed configuration.

In addition to manual manipulation and extension of surgical drape 1000 into the deployed configuration (e.g., by direct manual contact with rolled sheath portion 1040), a user may move pull member 1200 in the direction of deployment as indicated by arrow "D" in FIG. 3A. Movement of pull member 1200 in the direction of deployment imparts a force (e.g., rotational force) upon stiffener 1100 resulting in assisted movement of the second end 1030 of sheath 1010 away from the first end 1020 of sheath 1010, which aids the unrolling or unfurling of the rolled sheath portion 1040 into the deployed length "$L_2$" of sheath 1010.

With reference to FIGS. 3A and 3B, the progression of surgical drape 1000 from the un-deployed configuration to the deployed configuration will be further described. Surgical drape 1000 is provided to a user in the un-deployed configuration having the un-deployed length "$L_1$", with the second end 1030 of sheath 1010 positioned in close relation to the first end 1020 such that the rolled sheath portion 1040 is formed (as illustrated in FIG. 5E). Further, in the un-deployed configuration the second end 1204 of pull member 1200 extends from the rolled sheath portion 1040. As seen in FIG. 3A, surgical instrument 200, instrument drive unit 300, or the distal portion 9 of robotic arm 2 is inserted into the open cuff 1032 of sheath 1010 such that surgical drape 1000 is mounted thereon. Surgical drape 1000 may be oriented such that access port 1012 is aligned with the end effector 230 or elongate member 210 of surgical instrument 200. As seen in FIG. 3B, surgical drape 1000 is transitioned into the deployed configuration by moving the second end 1030 of sheath 1010 away from the first end 1020 in direction "D", such that the rolled sheath portion 1040 is unrolled or unfurled and the surgical drape assumes the deployed length "$L_2$". If assistance is required in deploying surgical drape 1000, pull member 1200 is additionally moved in direction "D" to facilitate movement of the second end 1030 of sheath 1010 away from the first end 1020.

During the transition from the un-deployed configuration to the deployed configuration, stiffener 1100 cooperatively moves, rotates, un-rolls, or unfurls with the second end 1030 of sheath 1010 away from the first end 1020, providing rigidity and support to the open cuff 1032. Once surgical drape 1000 is deployed to the desired deployed length "$L_2$", the second end 1030 of sheath 1010 may be cinched closed or secured to robotic arm 2 (e.g., by tying pull members 1200), thereby forming or maintaining a sterile barrier.

Alternatively, second end 1030 of sheath 1010 may be biased radially inward (indicated by arrows "R" in FIG. 4) such that once a user completes the deployment of surgical drape 1000 the second end 1030 of sheath 1010 cinches closed automatically to form or maintain a sterile barrier.

In accordance with an embodiment of the present disclosure, sheath 1010 may be loose fitting and substantially cylindrical over robotic arm 2, or may alternatively have a pre-set or pre-defined shape for specific surgical tools or robotic arms having defined dimensions.

With reference to FIGS. 1-7B, a method of maintain a sterile surgical environment will be disclosed. A surgeon, nurse, or other operator ("operator") initially inserts a portion of the surgical instrument or robotic surgical system 1 into the open cuff 1032 of sheath 1010 of surgical drape 1000 with sheath 1010 in the un-deployed configuration having the un-deployed length "$L_1$", thereby mounting surgical drape 1000 thereon. The operator next transitions the surgical drape 1000 to the deployed configuration by manually moving the second end 1030 of sheath 1010 away from the first end 1020. Further, the operator may move, or pull on, the pull member 1200 away from the first end 1020 of sheath 1010 to aid in the transition to the deployed configuration. Once the deployed length "$L_2$" of the sheath 1010 is achieved, or a desired or sufficient length of the surgical instrument 200 or robotic surgical system 1 is covered, the second end 1030 is cinched closed to create or maintain a sterile barrier. It should be appreciated that the deployed length "$L_2$" is dependent upon the operator's desired area of coverage based on, for example, the surgical procedure or the instrument being used wherein a sterile barrier is desired.

Persons skilled in the art will understand that the structures and methods specifically described herein and shown in the accompanying figures are non-limiting exemplary embodiments, and that the description, disclosure, and figures should be construed merely as exemplary of particular embodiments. It is to be understood, therefore, that the present disclosure is not limited to the precise embodiments described, and that various other changes and modifications may be effected by one skilled in the art without departing from the scope or spirit of the disclosure. Additionally, the elements and features shown or described in connection with certain embodiments may be combined with the elements and features of certain other embodiments without departing from the scope of the present disclosure, and that such modifications and variations are also included within the scope of the present disclosure. Accordingly, the subject matter of the present disclosure is not limited by what has been particularly shown and described.

What is claimed is:

1. A surgical drape for a surgical device, the surgical drape comprising:
    a sheath including a first closed end and a second open end adapted for insertion of a surgical instrument therein, wherein the sheath is transitionable between an un-deployed configuration wherein the second open end is spaced relatively close to the first closed end and a deployed configuration wherein the second open end is spaced relatively away from the first closed end;
    a stiffener secured adjacent the second open end of the sheath; and
    a pull member including a first end coupled to the stiffener, and a second free end, a length of the pull member wrapped around the stiffener in the un-deployed configuration of the sheath and unwrapped from the stiffener in the deployed configuration of the sheath, wherein the second free end of the pull member is accessible in both the deployed and un-deployed configurations of the sheath.

2. The surgical drape of claim 1, wherein the sheath is at least in part substantially cylindrical, and the first closed end is generally hemispherical.

3. The surgical drape of claim 1, wherein the second open end of the sheath is rolled onto itself towards the first closed end of the sheath in the un-deployed configuration.

4. The surgical drape of claim 1, wherein the sheath is fabricated from a flexible material.

5. The surgical drape of claim 1, wherein the stiffener is hourglass shaped.

6. The surgical drape of claim 1, further including a pull tab disposed at the second free end of the pull member.

7. The surgical drape of claim 1, further including at least one access port formed adjacent the first closed end of the sheath.

8. The surgical drape of claim 1, wherein the second open end of the sheath is biased radially inward.

9. The surgical drape of claim 1, further comprising a plurality of stiffeners and a plurality of pull members, the plurality of stiffeners radially disposed about the second open end of the sheath.

10. A robot surgical assembly comprising:
    a robotic arm; and
    a surgical drape, the surgical drape including:
        a sheath including a first closed end and a second open end adapted for insertion of the robotic arm therein, wherein the sheath is transitionable between an un-deployed configuration wherein the second open end is spaced relatively close to the first closed end and a deployed configuration wherein the second open end is spaced relatively away from the first closed end;
        a stiffener secured adjacent the second open end of the sheath;
        a pull member including a first end coupled to the stiffener, and a second free end, a length of the pull member wrapped around the stiffener in the un-deployed configuration of the sheath and unwrapped from the stiffener in the deployed configuration of the sheath, wherein the second free end of the pull member is accessible in both the deployed and un-deployed configurations of the sheath; and
        at least one access port formed adjacent the first closed end of the sheath;
    wherein the sheath provides a sterile barrier between the robotic arm and an external environment.

* * * * *